US00PP13874P39

(12) United States Plant Patent
Rowe

(10) Patent No.: US PP13,874 P3
(45) Date of Patent: Jun. 10, 2003

(54) COOKING BANANA PLANT 'FHIA-25'

(75) Inventor: Phillip Ray Rowe, La Lima (HN)

(73) Assignee: Fundación Hondureña de Investigación Agricola, San Pedro Sula (HN)

( * ) Notice: Subject to any disclaimer, the term of this patent is extended or adjusted under 35 U.S.C. 154(b) by 0 days.

(21) Appl. No.: 09/799,208

(22) Filed: Mar. 5, 2001

(65) Prior Publication Data

US 2002/0124287 P1 Sep. 5, 2002

(51) Int. Cl.[7] ..... A01H 5/00
(52) U.S. Cl. ..... Plt./160
(58) Field of Search ..... Plt./160

(56) References Cited

U.S. PATENT DOCUMENTS

PP8,983 P 11/1994 Rowe ..... Plt./33.1
PP9,791 P 2/1997 Rowe ..... Plt./33.1

*Primary Examiner*—Bruce R. Campell
*Assistant Examiner*—June Hwu
(74) *Attorney, Agent, or Firm*—Garvey, Smith, Nehrbass & Doody, L.L.C.; Seth M. Nehrbass

(57) ABSTRACT

This new and distinct variety of cooking banana plant has both *Musa acuminata* and *Musa balbisiana* in its pedigree. Its Latin name is *Musa acuminata×balbisiana* group AAB. AA representing two genomes of *M. acuminata* and B representing one genome of *M. balbisiana*. It has the following unique combination of desirable features:

1. A high level of resistance to *Mycosphaerella fijiensis,* causal fungus of the black Sigatoka leaf spot disease.
2. A dwarf plant height that enables it to withstand strong winds.
3. A strong root system which makes it a hardy plant under marginal water and soil conditions.
4. Large bunch sizes that are frequently greater than 45.0 kg.
5. Green fruit has a very good flavor and texture when boiled (as thick slices) or fried (as thin slices).
6. Green fruit that is easy to peel and exudes very little latex when peeled.
7. Harvested mature green fruit that has a long green life.

2 Drawing Sheets

LATIN NAME OF THE GENUS AND SPECIES OF THE PLANT CLAIMED

This triploid plant has both *Musa acuminata* and *Musa balbisiana* in its pedigree. This triploid hybrid is the product of an inter-specific cross between an improved hybrid tetraploid (AABB) type Bluggoe and an improved diploid (AA) of *Musa acuminata*. Its Latin name is *Musa acuminata×balbisiana* group AAB. AA representing two genomes of *M. acuminata* and B representing one genome of *M. balbisiana*.

VARIETY DENOMINATION

'FHIA-25'.

BACKGROUND OF THE INVENTION

This new variety was developed at the Fundación Hondureña de Investigación Agrícola (FHIA) in La Lima, Honduras from a cross made in 1995. It was selected in 1997 from several first-generation seedlings from the cross SH-3648×SH-3142 (both unpatented and both developed from accessions and breeding lines which are unpatented and are in the FHIA germplasm collection). SH-3648, which was developed by inventor, is a dwarf, bred tetraploid that is resistant to the black Sigatoka leaf spot disease. The pedigree of SH-3648 is II-408 and I-63→SH-2952×SH-2741→SH-3386×SH-3362→SH-3648. The two original II-408 and I-63 parental lines are the 'Gaddatu' (ABB) triploid clone from the Philippines and a *Musa balbisiana* (BB) diploid clone of unknown origin that was collected in Costa Rica, respectively. SH-2741 is a dwarf, bred diploid which was derived from AVP-45×AVP-23→SH-90×II-334→SH-2518×II-158→SH-2741. The AVP-45, AVP-23, II-334 and II-158 parental lines are a wild *Musa acuminata* subsp. *zebrina* diploid accession from Java, a 'Robusta' Cavendish triploid clone that was collected in Jamaica, a wild *Musa acuminata* subsp. *siamea* diploid from Malaysia, and a parthenocarpic *Musa acuminata* subsp. *errans* diploid from North Borneo, respectively. The SH-3362 diploid parental line of SH-3648 was selected from a segregating population derived from SH-3142×SH-3217. The SH-3142 diploid, which was developed by inventor and is the female parent of SH-3362 and the male parent of 'FHIA-25', was derived by crossing the SH-1734 bred diploid onto the 'Pisang Jari Buaya' natural diploid that was collected from Papua New Guinea. The diploids which are in the pedigree of SH-1734 are the 'Lidi' and 'Sinwobogi' parthenocarpic clones and a *Musa acuminata* subsp. *errans* wild type that were collected in Sumatra, Irian Jaya, and the Philippines, respectively. The SH-3217 parent of SH-3362 is a complex bred diploid, which has in its pedigree the parthenocarpic 'Guyod', 'Tjau Lagada', and 'Sinwobogi' natural diploids and a wild *Musa acuminata* subsp. *malaccensis* accession from the Philippines, Java, Irian Jaya, and Malaysia, respectively. 'FHIA-25' was selected as a hybrid triploid that maintained the dwarf plant stature and black Sigatoka resistance of its SH-3648 tetraploid parental line, but differs from SH-3648 in that it does not produce pollen. This absence of pollen results in seedless fruit, as compared to the seedy fruit of SH-3648, and this characteristic of 'FHIA-25' permits it to be cultivated as a commercial variety without concerns about seediness. 'FHIA-25' is also readily distinguished from SH-3648 by its rounded fruit shape, which closely resembles that of the reference Cavendish export banana, as compared to a more angular fruit shape for SH-3648.

This new cooking banana plant was asexually reproduced by corms as performed by inventor in the experimental farm of FHIA in La Lima, Cortés, Honduras and shows that all plant and fruit characteristics run true to the original selected plant and are identical in all respects.

BRIEF SUMMARY OF THE INVENTION

This new and distinct variety of cooking banana is a vigorous dwarf plant that produces large bunches of fruit. It is highly resistant to the black Sigatoka leaf spot disease, which is the most destructive and most costly disease of bananas and plantains worldwide. Interest in this new variety is that it is the first dwarf cooking banana that is highly resistant to black Sigatoka and has excellent cooking qualities as green fruit. This combination of exceptional plant and fruit characteristics make it a candidate for cultivation as a green cooking banana in areas where black Sigatoka has severely reduced the yields of the natural banana and plantain varieties that have traditionally been cultivated for production of green fruit for cooking.

BRIEF DESCRIPTION OF THE PHOTOGRAPHS

The accompanying photographic reproductions show typical specimens of the new cooking banana variety.

Figure 1:
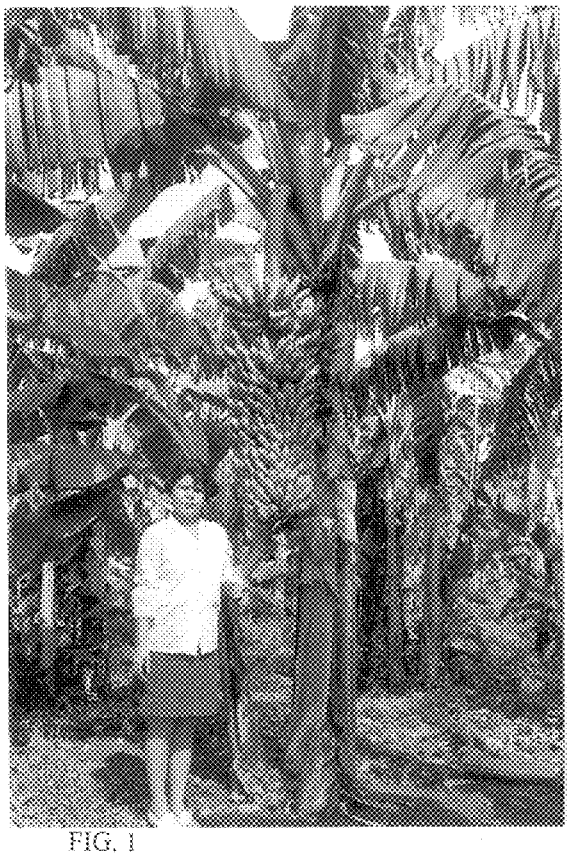
FIG. 1 shows a typical 'FHIA-25' Cooking Banana plant and a bunch one month before the fruit is ready for harvesting.
Figure 2:
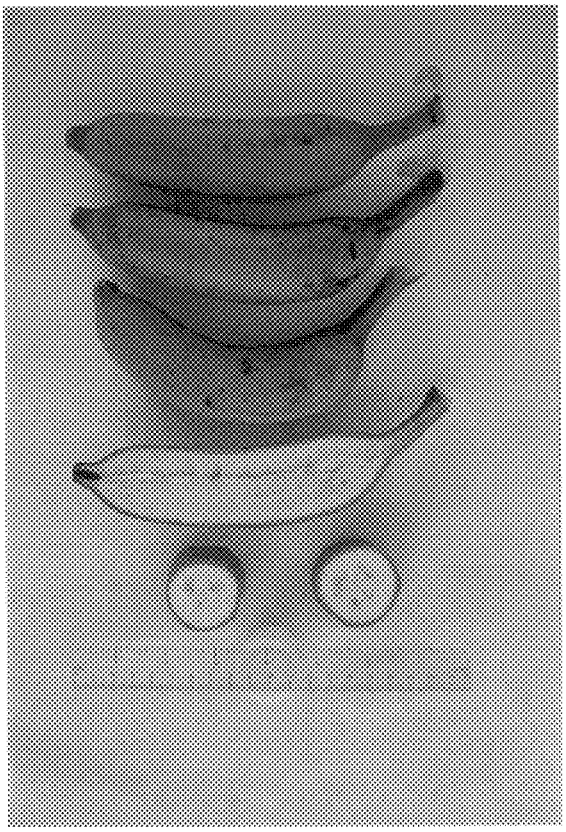
FIG. 2 shows representative whole fingers, a longitudinal section, and cross-sections of fruit at harvest stage of the new variety (marker is 20 cm)
Figure 3:
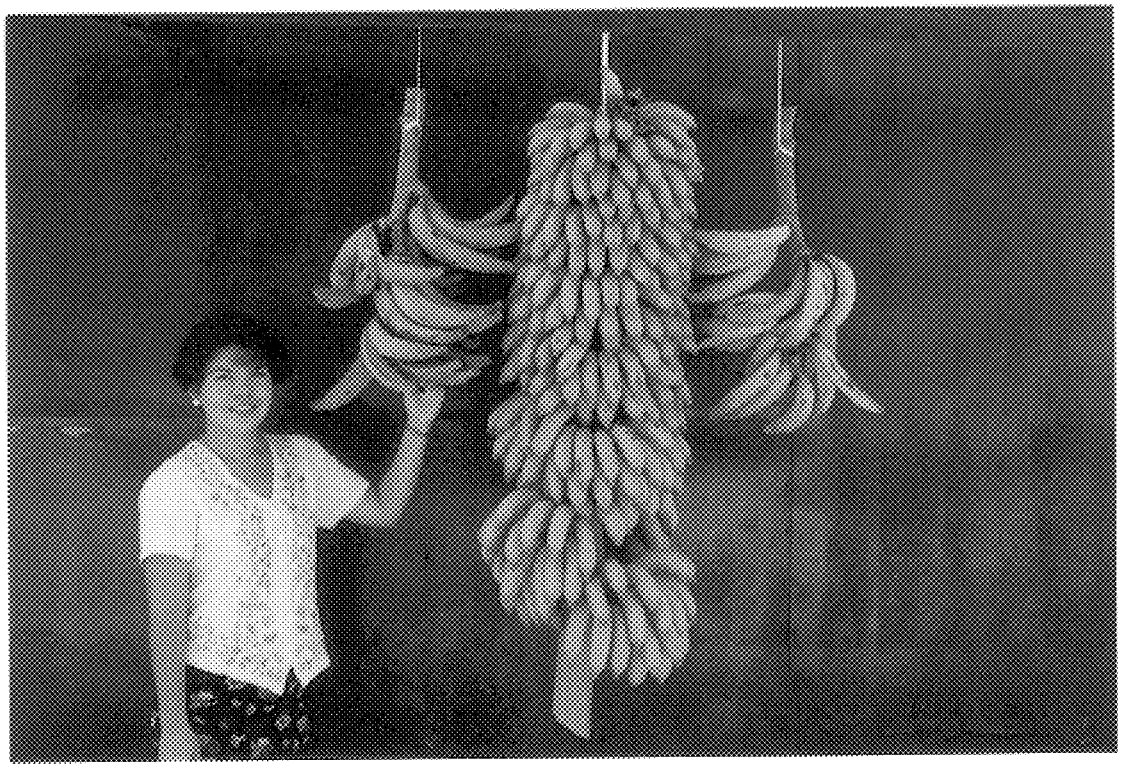

FIG. 3 shows a typical bunch of the 'FHIA-25' Cooking Banana (center) as compared to bunches of the universally cultivated 'False Horn' plantain variety (on both sides). These bunches are from plants which received no treatment for control of black Sigatoka, and this comparison is made because it is anticipated that one of the main uses of 'FHIA-25' will be to replace 'False Horn' in areas where black Sigatoka has severely reduced the yields of this plantain variety.

Figure 4:
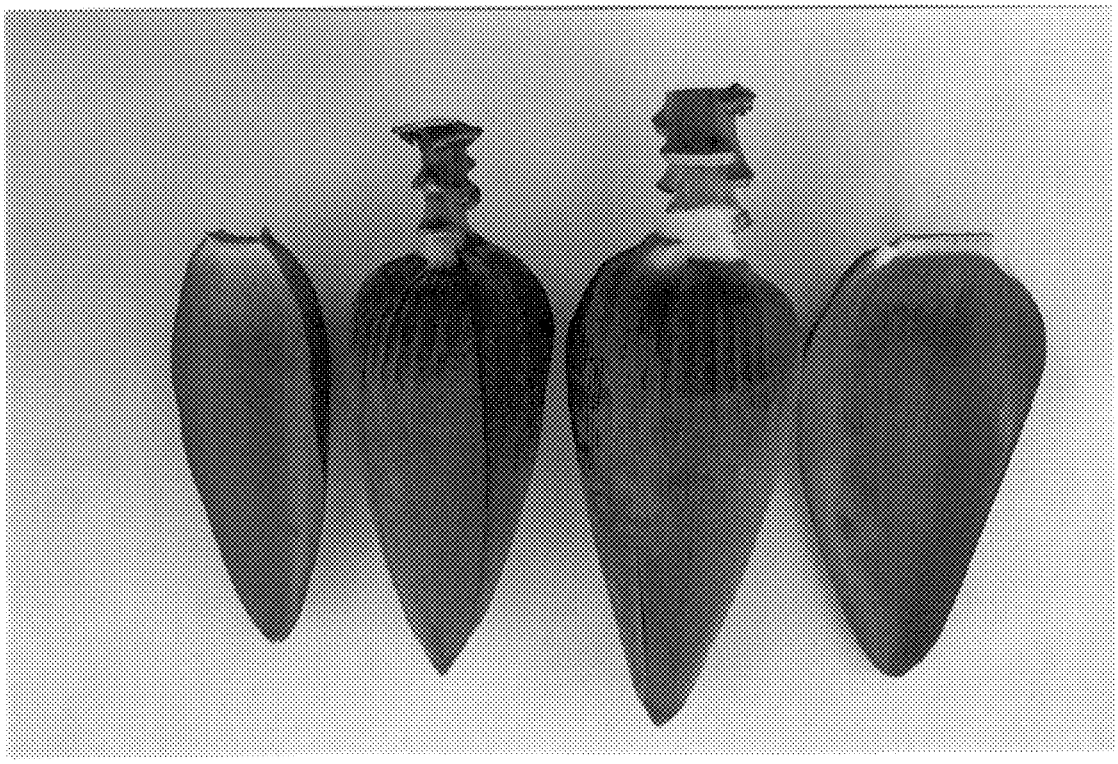

FIG. 4 shows detached newly formed male buds, with the outer bract removed before it lifts naturally, to depict botanically distinguishing size, shape and color differences in these plant parts of the 'Grand Nain' Cavendish export banana variety (left) as compared to 'FHIA-25'. Inside surface color of this outer bract for the new variety conforms to the color Red-Purple (3/10 5R).

The photographs were taken on fresh material and the colors are as nearly true as is reasonably possible in color representations of this type.

DETAILED BOTANICAL DESCRIPTION

The following is a detailed botanical description of the new and distinct variety of cooking banana plant, its flowers, foliage and fruit as based on observations of specimens grown in the FHIA experimental farm near La Lima, Cortés, Honduras. These descriptions are in accordance with the internationally standardized "Descriptors for Banana (Musa spp.)" elaborated by CIRAD/INIBAP/IPGRI (www.inibap.org). The color terminology is in accordance with the Munsell Color Chart for Plant Tissues.

Plant general appearance:
- *Ploidy.*—Triploid (AAB).
- *Leaf habit.*—Drooping.
- *Dwarfism.*—Dwarf type.

Pseudostems/suckers: (Data taken 450 days after transplanting at first ripe fruit.)
- *Pseudostem height.*—2.5 m.
- *Pseudostem appearance.*—Robust.
- *Pseudostem color.*—Green-yellow (8/4 2.5GY) base color with dark brown (3/2 10R), uneven blotches.
- *Pseudostem appearance.*—Shiny (not waxy).
- *Predominant underlying color of the pseudostem.*—Green-yellow (8/4 2.5GY).
- *Pigmentation of the underlying pseudostem.*—Pink-purple (4/6 10R).
- *Sap color.*—Tending toward Milky (8/2 5Y).
- *Wax on leaf sheaths.*—Moderately waxy.
- *Number of suckers.*—6.
- *Development of suckers.*—>¼ and <¾ of the height of the parent plant.
- *Position of suckers.*—Close to parent (growing at an angle).

Petioles/midribs/leaves: (Data taken on the 3$^{rd}$ fully unfolded leaf counting down from the top of the plant at 430 days — time of harvest — after transplanting.)
- *Blotches at the petiole base.*—Extensive pigmentation.
- *Color of blotches.*—Dark brown (3/2 10R).
- *Petiole canal of leaf three.*—Open with spreading margins.
- *Petiole margins.*—Winged and not clasping the pseudostem.
- *Wing appearance.*—Dry.
- *Wing color.*—(6/2 5YR).
- *Petiole margin color.*—Pink/purple (612 5YR).
- *Edge of petiole margin.*—With a color line along.
- *Petiole margin width.*—8 to 11 mm.
- *Leaf blade length.*—221 to 260 cm.
- *Leaf blade width.*—88 to 92 cm.
- *Petiole length.*—51 to 70 cm.
- *Color of upper leaf surface.*—Green (3/4 7.5 GY).
- *Appearance of upper leaf surface.*—Tending to dull.
- *Color of lower leaf surface.*—Green (5/6 7.5GY).
- *Appearance of lower leaf surface.*—Dull.
- *Wax on leaves.*—Very waxy.
- *Insertion point of leaf blades on petiole.*—Mostly symmetric.
- *Shape of leaf blade base.*—Both sides tapered in first leaves going to both rounded in later leaves.
- *Leaf corrugation.*—Few stripes.
- *Color of midrib dorsal surface.*—Pink-Purple (8/4 2.5 GY) at leaf emergence going to Green-yellow (8/4 2.5GY) as leaf matures.
- *Color of midrib ventral surface.*—Light green (7/6 2.5 GY).
- *Color of cigar leaf dorsal surface.*—Pink-Purple (6/4 2.5 GY) when rolled going to green when unrolled and mature.
- *Blotches on leaves of water suckers.*—Without blotches.

Inflorescence/male bud: (Data taken 330 days after transplanting at completion of flower emergence.)
- *Peduncle length.*—82 to 85 cm.
- *Empty nodes on peduncle.*—One to Two.
- *Peduncle width.*—7–12 cm.
- *Peduncle color.*—Medium green (5/8 5.6Y).
- *Peduncle hairiness.*—Slightly hairy.
- *Bunch position.*—Hanging vertically.
- *Bunch shape.*—Cylindrical when young going to truncated cone shape at maturity.
- *Bunch appearance.*—Compact.
- *Flowers that form the fruit.*—Female.
- *Fruits.*—Biseriate.
- *Rachis type.*—Present and male bud may be degenerated or persistent.

*Rachis position.*—Falling vertically.
*Rachis appearance.*—Neutral flowers.
*Male bud type.*—Normal (present).
*Male bud shape.*—Intermediate between lanceolate and ovoid.
*Male bud size.*—21 to 30 cm.

Bract: (Data taken 330 days after transplanting at completion of flower emergence.)
*Bract base shape.*—Small to intermediate shoulder.
*Bract base size.*—Average 6 cm for the part connected to the rachis.
*Bract apex shape.*—Intermediate between pointed apex and obtuse apex.
*Bract imbrications.*—Young bracts slightly overlap at apex of bud.
*Bract length.*—Average 30 cm at longest point.
*Bract width.*—Average 20 cm at widest point.
*Color of the bract external face.*—Purple (3/2 5RP).
*Color of the bract internal face.*—Red-Purple (3/10 5R).
*Color on the bract apex.*—Tinted with yellow (8/6 2.5Y).
*Color stripes on bract.*—Without discolored lines (not ridges) on the external face.
*Bract scars on rachis.*—Very prominent.
*Fading of color on bract base.*—Color homogenous.
*Male bract shape.*—Ovate.
*Male bract lifting.*—Lifting one or two at a time.
*Bract behaviour before falling.*—Revolute (rolling).
*Wax on the bract.*—Very waxy.
*Presence of grooves on the bract.*—Tending toward strongly grooved.

Male flowers: (Data taken 330 days after transplanting at completion of flower emergence.)
*Male flower behaviour.*—Falling after the bract.
*Compound tepal basic color.*—Cream (8/1 5Y).
*Compound tepal pigmentation.*—Red-Purple (4/10 5RP) spots on shoulder.
*Lobe color of compound tepal.*—Bright yellow (8/12 2.5Y).
*Lobe development of compound tepal.*—Developed.
*Free tepal color.*—Transparent white (8/1 5Y).
*Free tepal shape.*—Oval.
*Free tepal appearance.*—More or less smooth.
*Free tepal apex development.*—Developed.
*Free tepal apex shape.*—Filiform.
*Anther exsertion.*—25 mm.
*Filament color.*—Cream (8/2 5Y).
*Anther color.*—Cream (8/4 5Y).
*Pollen sacs color.*—Cream (8/4 2.5Y).
*Pollen vitality.*—Absent.
*Style basic color.*—White (8/1 5Y).
*Pigmentation on style.*—Purple (5/6 5RP).
*Style exsertion.*—15 mm.
*Style shape.*—Curved at the base.
*Stigma color.*—Cream (8/4 2.5Y).
*Ovary shape.*—Slightly arched.
*Ovary basic color.*—Light green (8/4 2.5GY).
*Ovary pigmentation.*—Very few or no visible signs of pigmentation.
*Dominant color of male flower.*—Cream (8/1 5Y) going to light Yellow (8/4 2.5GY).
*Irregular flowers.*—Absent.
*Arrangement of ovules.*—Two rowed.

Fruit: (Data taken at 430 days from transplanting at harvest.)
*Fruit position.*—Curved towards stalk.
*Number of fruits.*—15 average.
*Fruit length.*—21–25 cm.
*Fruit shape* (*longitudinal curvature*).—Straight in the distal part.
*Transverse section of fruit.*—Slightly ridged.
*Fruit apex.*—Bottle-necked.
*Remains of flower relicts at fruit apex.*—Persistent style.
*Fruit pedicel length.*—22 mm.
*Fruit pedicel width.*—10.5 mm.
*Pedicel surface.*—Hairless.
*Fusion of pedicels.*—Very partially or no visible sign of fusion.
*Immature fruit peel color.*—Light Green (6/8 7.5GY).
*Mature fruit peel color.*—Bright yellow (8/10 2.5Y).
*Fruit peel thickness.*—2.5 to 3.5 mm.
*Adherence of the fruit peel.*—Fruit peels easily.
*Cracks in fruit peel.*—Cracked.
*Pulp in fruit.*—With pulp.
*Pulp color before maturity.*—Cream (8/1 5Y).
*Pulp color at maturity.*—White (8/1 2.5 Y).
*Fruits fall from hands.*—Persistent.
*Fruit is eaten.*—Cooked green.
*Flesh texture.*—Soft.
*Predominant taste.*—Astringent.
*Main use.*—Cooking banana.
*Presence of seed with source of pollen.*—1 to 5.
*Seed surface.*—Wrinkled.
*Seed shape.*—Rounded (but not completely spherical).

Agronomic characteristics (averages taken during 1998–1999 for first crop in a plot of 10 plants with no control of diseases):
*Days from planting to first flowering.*—325.
*Number of leaves at flowering.*—13.
*Number of functional leaves* (*less than 15% of area necrotic*) *at flowering.*—3.
*Number of leaves at harvest.*—10.
*Number of functional leaves* (*less than 15% of area necrotic at harvest*).—9.
*Days from flowering until harvest.*—105.
*Bunch weight.*—40.0 kg.
*Number of hands.*—12.5.
*Finger length.*—14.1 cm.
*Number of fingers per bunch.*—214.
*Days from first flowering until second flowering.*—250.

This cooking banana plant and its fruit described above may vary slightly in detail due to cultural practices, soil types and climatic conditions under which the variety may be grown; the present description is that of the variety grown under the ecological conditions prevailing on the FHIA experimental station near La Lima, Cortés, Honduras.

I claim:

1. A new and distinct variety of cooking banana plant, substantially as illustrated and described, which is a dwarf plant and has a high level of resistance to the black Sigatoka leaf spot disease; the green fruit is further characterized by having a very good flavour and texture when boiled, to having a long green life after harvest, and to being easy to peel for cooking.

* * * * *